United States Patent
Okada et al.

(10) Patent No.: US 6,264,472 B1
(45) Date of Patent: Jul. 24, 2001

(54) METHOD FOR SETTING DENTAL GLASS IONOMER CEMENT

(75) Inventors: Kaori Okada; Kazuo Hirota, both of Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/631,117

(22) Filed: Aug. 2, 2000

(30) Foreign Application Priority Data

Aug. 10, 1999 (JP) .................................................. 11-226354

(51) Int. Cl.$^7$ ....................................................... A61C 5/00
(52) U.S. Cl. .......................................... 433/228.1; 523/116
(58) Field of Search .......................... 433/29, 226, 228.1; 523/116, 115

(56) References Cited

U.S. PATENT DOCUMENTS

| | | | |
|---|---|---|---|
| 4,524,824 | 6/1985 | Shimokobe et al. | 106/35 |
| 4,591,384 | 5/1986 | Akahane et al. | 106/35 |
| 4,632,824 | 12/1986 | Hirota et al. | 424/49 |
| 4,647,600 | 3/1987 | Kawahara et al. | 523/116 |
| 4,652,953 | 3/1987 | Sakurai et al. | 360/106 |
| 4,775,592 | 10/1988 | Akahane et al. | 428/406 |
| 4,900,697 | 2/1990 | Akahane et al. | 501/57 |
| 4,936,775 * | 6/1990 | Bennett | 433/220 |
| 5,063,257 | 11/1991 | Akahane et al. | 523/116 |
| 5,520,725 * | 5/1996 | Kato et al. | 106/35 |
| 5,962,550 | 10/1999 | Akahane et al. | 523/116 |
| 6,063,832 * | 5/2000 | Yuhda et al. | 523/116 |

\* cited by examiner

*Primary Examiner*—John J. Wilson
*Assistant Examiner*—Melba Bumgarner
(74) *Attorney, Agent, or Firm*—Oblon, Spivak, McClelland, Maier & Neustadt, P.C.

(57) ABSTRACT

A method for setting a dental glass ionomer cement by means of irradiation with a light to accelerate initial setting, the cement comprising a fluoroaluminosilicate glass powder, a polycarboxylic acid and water, is disclosed. Further, the light to be irradiated in the method for setting the dental glass ionomer cement is preferably a light having a wavelength in the range of from 320 to 3,000 nm, and the irradiation intensity and irradiation time of the light are preferably from 200 to 3,000 mW/cm$^2$ and from 1 to 180 seconds, respectively. According to the method for setting the dental glass ionomer cement of this invention, the time for sensitization to water and the initial setting time can be shortened, without necessity of particularly performing an operation for preventing the sensitization to water with a varnish or the like.

9 Claims, No Drawings

METHOD FOR SETTING DENTAL GLASS IONOMER CEMENT

BACKGROUND OF THE INVENTION

1. Field of the Invention

The present invention relates to a method for setting a dental glass ionomer cement that is used for restoring a tooth in the dental remedy or the like.

2. Description of the Conventional Art

Variety of dental cements is generally used in the remedy of teeth. Representative examples include a zinc phosphate cement in which zinc oxide is reacted with phosphoric acid, a carboxylate cement in which zinc oxide is reacted with a polycarboxylic acid, a resin cement using the polymerization of an acrylic monomer, a calcium hydroxide cement in which calcium hydroxide is reacted with an oily component, a zinc oxide eugenol cement in which zinc oxide is reacted with eugenol, and a glass ionomer cement using a fluoroaluminosilicate glass powder and a polycarboxylic acid.

These dental cements are widely used in the dental remedy. More specifically, they are widely used for cementing a dental prosthesis such as a crown, an inlay, and a bridge, or cementing an orthodontic device and a dentin, for filling a tooth cavity, for sealing pit and fissure in enamel, for lining, and for rebuilding base and core.

Of these, the dental glass ionomer cement has a superior biocompatibility, it has adhesive properties to a tooth structure and a set cement thereof is translucent and superior in esthetics, and it has an advantage in that it gradually releases after setting fluorine with a lapse of time, thereby a caries resistant function can be expected. Accordingly, the dental glass ionomer cement is a dental cement that is most generally used in the wide variety of applications in the dentistry.

This dental glass ionomer cement is a dental cement in which a a fluoroaluminosilicate glass powder and a polycarboxylic acid as the major components cause a setting reaction in the presence of water and are set. More specifically, an aqueous polyacrylic acid solution exerts the fluoroaluminosilicate glass powder to liberate metal ions (such as alkali metal ions, alkaline earth metal ions, and aluminum ion) in the glass, which then undergo ionic bonding to a carboxyl group of the polyacrylic acid, to form a crosslinking structure, thereby causing gelation and setting (this reaction will be hereinafter sometimes referred to as "ionomer reaction"). And, it is also known that the dental ionomer cement continues to cause the ionomer reaction after the initial setting, so that the compressive strength of a set cement thereof gradually increases for one year after the start of the setting.

In addition, there is developed a resin reinforcement type of a dental glass ionomer cement in which a dental glass ionomer cement is compounded with a polymerizable monomer, thereby utilizing a polymerization reaction with the monomer in combination with the ionomer reaction. This resin reinforcement type of a dental glass ionomer cement is improved in terms of mechanical strengths such as bending strength and adhesive properties to a tooth structure, as compared with the conventional dental glass ionomer cement that causes the setting only relying upon the ionomer reaction.

The method for setting the dental glass ionomer cement is generally carried out in the following manner. That is, the fluoroaluminosilicate glass powder and the aqueous polyacrylic acid solution are respectively weighed and mixed in an appropriate ratio on a mixing pad for exclusive use by means of an instrument such as a spatula; or prescribed amounts of the fluoroaluminosilicate glass powder and the aqueous polyacrylic acid solution are respectively weighed and accommodated in a capsule so that the fluoroaluminosilicate glass powder and the aqueous polyacrylic acid solution are isolated from each other, and at the time of use, the partition is broken to mix fluoroaluminosilicate glass powder and the aqueous polyacrylic acid solution with each other by means of a capsule mixer or the like. The resulting mixture is filled in or applied on a cavity or pit and fissure in enamel. Some products which is also available include a hydraulic dental ionomer in which a mixture of a fluoroaluminosilicate glass powder and a polyacrylic acid powder is provided to undergo setting upon mixing with water. Therefore, the glass ionomer cements according to the present invention comprise the fluoroaluminosilicate glass powder, the polycarboxylic acid and water for setting.

As described above, since the dental glass ionomer cement uses the ionomer reaction, a time is required for the initial setting. Thus, it is impossible to perform the next clinical operation until the initial setting. Further, it is pointed out that the dental glass ionomer cement has a defect called as sensitization to water: that is, before or after the initial setting, when a surface of the dental glass ionomer cement mixture comes into contact with water, metal ions elute during the setting reaction, or the content of water increases, whereby the cement surface becomes cloudy or brittle, ultimately leading to a decrease of the surface performance after the setting. This is caused due to the ionomer reaction of the dental glass ionomer cement which is an acid/base reaction between the fluoroaluminosilicate glass (base) and the polycarboxylic acid (acid radical) in the presence of water and is sensitively influenced by water from outside.

In order to overcome this defect, the following measure was carried out. That is, the dental glass ionomer cement before the initial setting is filled and applied carefully so that it does not come into contact with water from outside such as saliva and then a moistureproof material called as a varnish such as resin-based materials is applied and dried to form a coating film on the dental glass ionomer cement surface, so as to effect a moistureproofing for 20 to 25 minutes during the initial setting.

SUMMARY OF THE INVENTION

An object of the present invention is to provide a method for setting a dental glass ionomer cement, upon which the dental glass ionomer cement is made hardly sensitive to water even without preventing sensitization to water with a varnish, and the time for sensitization to water and the initial setting time can be shortened.

We, the present inventors, paid attention to the matter that the ionomer reaction used for the dental glass ionomer cement is sensitive to and reactive with a change of the temperature so that the setting reaction is rapidly promoted even by a slight temperature increase, and made extensive and intensive investigations. As a result, it has been found that the time for sensitization to water and the initial setting time can be shortened by irradiating the dental glass ionomer cement with a light, leading to the accomplishment of the present invention.

More specifically, the present invention relates to method for setting a dental glass ionomer cement by means of irradiation with a light to accelerate initial setting, the cement comprising a fluoroaluminosilicate glass powder, a polycarboxylic acid and water.

DETAILED DESCRIPTION OF THE INVENTION

In the method for setting a dental glass ionomer cement according to the present invention, it is preferred that the light to be irradiated has a wavelength in the range of from 320 to 3,000 nm, the irradiation intensity of the light is in the range of from 200 to 3,000 mW/cm$^2$, and the irradiation time of the light is in the range of from 1 to 180 seconds.

The method for setting a dental glass ionomer cement according to the present invention is a method for setting the above-described dental glass ionomer cement by means of irradiation with a light to accelerate initial setting, the cement comprising the fluoroaluminosilicate glass powder, the polycarboxylic acid and water. As compared with a setting method in which the irradiation with a light is not performed, the setting method according to the present invention enables to shorten the time for sensitization to water and the initial setting time only by undergoing the irradiation with a light for from several seconds to several minutes without particularly performing an operation for preventing the sensitization to water including application of a varnish and drying. Further, according to the setting method of the present invention, since the composition of the dental glass ionomer cement is not changed, the superior characteristics of the dental ionomer cement can be kept as they stand.

Prior to the present invention, a phenomenon in which, when the dental glass ionomer cement comprising the fluoroaluminosilicate glass powder, the polycarboxylic acid and water is irradiated with a light, the ionomer reaction is promoted, whereby the dental glass ionomer cement sets, has not been drawing an attention, in spite of the fact that a photopolymerization type dental ionomer cement that undergoes initial setting upon photopolymerization has been used over a long period of time.

The reason for this may be considered as follows. In the dental field, it has been conventionally widely carried out to irradiate a photopolymerization type dental composite resin or photopolymerization type dental glass ionomer cement with a light to undergo photopolymerization for setting. These dental materials always contain a photopolymerization initiator such as camphor quinone and a polymerizable monomer. And, the photopolymerization initiator is activated by the light irradiation, thereby undergoing a polymerization reaction of the polymerizable monomer to set the resin or cement. Accordingly, the light irradiation was essential.

On the other hand, in the method for setting the dental glass ionomer cement according to the present invention, the temperature of the dental glass ionomer cement comprising the fluoroaluminosilicate glass powder, the polycarboxylic acid and water is increased upon irradiation with a light, thereby promoting the ionomer reaction to set the dental glass ionomer cement. Accordingly, a large advantage is given to the dental glass ionomer cement having neither photopolymerization initiator nor polymerizable monomer compounded therewith.

The dental glass ionomer cement that is used in the present invention refers to a whole of cements having a mechanism in which the fluoroaluminosilicate glass powder and the polycarboxylic acid cause a setting reaction (i.e., the ionomer reaction) in the presence of water, whereby the cement sets. The setting method according to the present invention is effective to conventional type dental glass ionomer cements not containing a polymerizable monomer, in which the setting occurs only by the ionomer reaction; dental glass ionomer cements for base, comprising a conventional type dental glass ionomer cement having a metal added thereto; resin reinforcement type dental glass ionomer cements comprising a conventional type dental glass ionomer cement having a polymerizable monomer compounded therewith; and the like.

The fluoroaluminosilicate glass powder that is used in the general dental glass ionomer cement has a major composition of from 10 to 25% by weight of $Al^{3+}$, from 5 to 30% by weight of $Si^{4+}$, from 1 to 30% by weight of $F^-$, from 0 to 20% by weight of $Sr^{2+}$, from 0 to 20% by weight of $Ca^{2+}$, and from 0 to 10% by weight of an alkali metal ion (e.g., $Na^+$, $K^+$, etc.), based on the total weight of the glass. The raw material containing these metal ions is mixed and molten, and then cooled and pulverized to prepare a powder having a mean particle size of from about 0.02 to 20 µm.

The polycarboxylic acid as referred to herein is a polymer of an α,β-unsaturated monocarboxylic acid or of an α,β-unsaturated dicarboxylic acid and is generally a copolymer or homopolymer having a weight average molecular weight of from 5,000 to 40,000, of acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, or the like.

In addition, if desired, the general dental glass ionomer cement is added with known polymerization inhibitors, ultraviolet light absorbers, plasticizers, coloring pigments, antioxidants, fungicides, surfactants, etc.

Examples of the device that can be used for the light irradiation in the present invention are those using a light source capable of emitting a light having a wavelength ranging from 320 to 3,000 nm, which are widely used in the dentistry at present, including irradiation machine of an infrared light, a visible light, or a ultraviolet light. When the wavelength is shorter than 320 nm, a detrimental effect to bodies becomes strong, and hence, such is not preferred. On the other hand, a light having a wavelength region exceeding 3,000 nm is low in the action to promote the setting reaction of the dental glass ionomer cement. Of these, it is easy and desired for a dentist to use a visible light irradiation machine capable of effecting irradiation with a light having a wavelength of from 390 to 510 nm, which is generally used for polymerizing the resin reinforcement type glass ionomer cement or composite resin.

In the method for setting the dental glass ionomer cement according to the present invention, since the irradiation with a light having a wavelength ranging from 320 to 3,000 nm increases the temperature of the dental glass ionomer cement within an appropriate period of time and promotes the setting reaction, it is preferred to carry out the light irradiation at an irradiation intensity of at least 200 mW/cm$^2$. Taking into account the operability, it is preferred that the time for effecting the light irradiation is as short as possible. However, in order to obtain the advantage by the light irradiation, in the case where the above-described light irradiation machine is used, the light irradiation time is required to be at least one second. On the other hand, since the initial setting time of the general dental glass ionomer cement is from 4 minutes to 8 minutes, it is preferred to complete the light irradiation within 180 seconds.

The use example of the method for setting the dental glass ionomer cement according to the present invention will be described below.

1. First of all, a tooth in which a caries or the like is removed by cavity preparation, etc. to form a cavity is filled or applied with a dental glass ionomer cement, which has been mixed by a hand, a capsule mixer, etc. In the case where the dental glass ionomer cement is used for filling, the fairly hard mixture is filled in the cavity, or in the case where it is used as a sealant, the cement having high fluidity is applied to pit and fissure in enamel.

2. Next, the filled or applied dental glass ionomer cement is irradiated with a light. Although, at the time of completion of the light irradiation, it is not always necessary that the dental glass ionomer cement's initial setting is completed, in the case that the dental glass ionomer cement is used as the sealant, it is preferred that its initial setting is completed.

3. After the dental glass ionomer cement used for filling has completed initial setting, the surface is polished to effect final finishing. While the timing of the polishing varies depending on the type of the material to be used, in the case that the light irradiation has been performed, the polishing can be carried out earlier than usual because the period of the time for sensitization to water is apparently more shortened as compared with the case that the light irradiation has not been performed.

The method for setting the dental glass ionomer cement according to the present invention will be described in more detail with reference to the following Examples.

Incidentally, all of the four dental glass ionomer cements used in the Examples and Comparative Examples are a dental glass ionomer cement that sets only by the reaction of the fluoroaluminosilicate glass powder and the polycarboxylic acid in the presence of water, which does not contain a polymerizable monomer.

EXAMPLE 1

A commercially available type dental glass ionomer cement (a product name: Fuji Ionomer Type II, made by GC Corporation) was mixed in a weight ratio of powder to liquid of 2.7:1 for 30 seconds, and then filled in an acrylic resin-made ring having a diameter of 10 mm and a height of 5 mm. A transparent celluloid plate was put on and brought into press contact with the acrylic resin-made ring, and one minute after the start of mixing, a light was irradiated on the celluloid plate for 20 seconds by means of a visible light irradiation machine (a product name: GC LABOLIGHT VL-II, manufactured by GC Corporation, wavelength from 400 to 520 nm, irradiation intensity 780 mW/cm$^2$). Immediately after the light irradiation, the celluloid plate was removed, and the sample together with the acrylic resin-made ring was immersed in water at 37° C. Other samples were each irradiated with a light in the same manner and allowed to stand in a room for 2 minutes (in this case, 40 seconds after the light irradiation), 3 minutes, 4 minutes, and sequentially, every one minute after the start of mixing until 30 minutes. Then, the samples were each immersed in water at 37° C. Twenty-four hours later, each sample was taken out from water, dried and then visually observed for the presence of cloudiness on the sample surface by the sensitization to water. And, a time when the cloudiness of the sample had become not observed after the start of mixing was taken as a time for sensitization to water. Further, the time for sensitization to water was measured in the same manner, except that the light irradiation time was changed to 40 seconds and 60 seconds, respectively. The results obtained are shown in Table 1.

With respect to the type dental glass ionomer cement mixed in the above-described method, the light irradiation was carried out for 20 seconds, 40 seconds, and 60 seconds, respectively. And, the initial setting time from the start of mixing including the light irradiation time was measured in accordance with "5.4 Setting Time Test" of JIS T-6607 (dental glass polyalkenol cement). The results obtained are also shown in Table 1.

EXAMPLE 2

A commercially available type dental glass ionomer cement (a product name: Ketac-Cem, made by Espe AG) was mixed in a weight ratio of powder to liquid of 2:1 and evaluated in terms of the time for sensitization to water of the sample surface and the initial setting time in the same manner as in Example 1. The results obtained are shown in Table 1.

EXAMPLE 3

A commercially available type dental glass ionomer cement (a product name: Fuji IX GP, made by GC Corporation) was mixed in a weight ratio of powder to liquid of 3.6:1 and evaluated in terms of the time for sensitization to water of the sample surface and the initial setting time in the same manner as in Example 1. The results obtained are shown in Table 1.

EXAMPLE 4

A commercially available type dental glass ionomer cement (a product name: Ketac-Molar (capsule), made by Espe AG) was mixed by means of a Capsule Mixer CM-1 (manufactured by GC Corporation) and evaluated in terms of the time form sensitization to water of the sample surface and the initial setting time in the same manner as in Example 1. The results obtained are shown in Table 1.

TABLE 1

|  | Time for sensitization to water | | | Initial setting time | | |
| --- | --- | --- | --- | --- | --- | --- |
|  | Light irradiation for 20 seconds | Light irradiation for 40 seconds | Light irradiation for 60 seconds | Light irradiation for 20 seconds | Light irradiation for 40 seconds | Light irradiation for 60 seconds |
| Example 1 | 10 minutes | 7 minutes | 2 minutes | 4 minutes | 3 minutes | At the time of completion of the irradiation, initial setting already occurred. |
| Example 2 | 3 minutes | Since just after the irradiation, no sensitization | Since just after the irradiation, no sensitization | 2 minutes and 15 seconds | At the time of completion of the irradiation, initial setting | At the time of completion of the irradiation, initial setting |

TABLE 1-continued

|  | Time for sensitization to water | | | Initial setting time | | |
|---|---|---|---|---|---|---|
|  | Light irradiation for 20 seconds | Light irradiation for 40 seconds | Light irradiation for 60 seconds | Light irradiation for 20 seconds | Light irradiation for 40 seconds | Light irradiation for 60 seconds |
| Example 3 | 5 minutes | to water occurred. Since just after the irradiation, no sensitization to water occurred. | to water occurred. Since just after the irradiation, no sensitization to water occurred. | 3 minutes and 45 seconds | already occurred. At the time of completion of the irradiation, initial setting already occurred. | already occurred. At the time of completion of the irradiation, initial setting already occurred. |
| Example 4 | 12 minutes | 8 minutes | 5 minutes | 4 minutes and 30 seconds | 3 minutes and 45 seconds | 3 minutes |

Comparative Examples 1 to 4

Using the same commercially available dental glass ionomer cements as in Examples 1 to 4, the tests were carried out in the same manner as in Example 1, except that no light irradiation was carried out and that the samples were each immersed in water at 37° C. for 10 minutes, 11 minutes, and sequentially, every one minute after the start of mixing until 30 minutes, to measure the time for sensitization to water and the initial setting time. The results obtained are summarized and shown in Table 2.

TABLE 2

|  | Time for sensitization to water | Initial setting time |
|---|---|---|
| Comparative Example 1 | 20 minutes | 7 minutes |
| Comparative Example 2 | 15 minutes | 6 minutes |
| Comparative Example 3 | 17 minutes | 6 minutes and 30 seconds |
| Comparative Example 4 | 25 minutes | 7 minutes and 45 seconds |

As is clear from the Examples and Comparative Examples, it can be understood that since the method for setting the dental glass ionomer cement according to the present invention can promote the initial setting of the dental glass ionomer cement, it is effective for preventing the sensitization to water without particularly performing an operation for preventing the sensitization to water with a varnish or the like.

In addition, since, by the method for setting the dental glass ionomer cement according to the present invention, the time for sensitization to water and the initial setting time can be shortened by the time for irradiation with a light, an operator can control set up the initial setting time. Accordingly, this invention is very valuable in contributing to the dental remedy.

What is claimed is:

1. A method for setting a dental glass ionomer cement comprising a fluoroaluminosilicate glass powder, a polycarboxylic acid and water, wherein said dental glass ionomer cement contains no photopolymerization initiator, which comprises irradiating said dental glass ionomer cement with light to accelerate initial setting.

2. The method according to claim 1, wherein said light has a wavelength in the range of from 320 to 3,000 nm.

3. The method according to claim 1 or 2, wherein said light has an irradiation intensity in the range of from 200 to 3,000 mW/cm$^2$, and an irradiation time in the range of 1 to 180 seconds.

4. The method according to claim 1, wherein said dental glass ionomer cement further contains no polymerizable monomer.

5. The method according to claim 1, wherein said fluoroaluminosilicate glass powder has from 10 to 25% by weight of $Al^{3+}$, from 5 to 30% by weight of $Si^{4+}$, from 1 to 30% by weight of $F^-$, from 0 to 20% by weight of $Sr^{2+}$, from 0 to 20% by weight of $Ca^{2+}$ and from 0 to 10% by weight of an alkali metal ion, based on the total weight of said fluoroaluminosilicate glass powder.

6. The method according to claim 1, wherein said polycarboxylic acid is a homopolymer or copolymer of an α, β-unsaturated monocarboxylic acid or an α, β-unsaturated dicarboxylic acid.

7. The method according to claim 1, wherein said polycarboxylic acid is a homopolymer or copolymer of an acid selected from the group consisting of acrylic acid, methacrylic acid, 2-chloroacrylic acid, 3-chloroacrylic acid, aconitic acid, mesaconic acid, maleic acid, itaconic acid, fumaric acid, glutaconic acid and citraconic acid.

8. The method according to claim 1, wherein said fluoroaluminosilicate glass powder has from 10 to 25% by weight of $Al^{3+}$, from 5 to 30% by weight of $Si^{4+}$, from 1 to 30% by weight of $F^-$, from 0 to 20% by weight of $Sr^{2+}$, from 0 to 20% by weight of $Ca^{2+}$ and from 0 to 10% by weight of an alkali metal ion, based on the total weight of said fluoroaluminosilicate glass powder and said polycarboxylic acid is is a homopolymer or copolymer of an α, β-unsaturated monocarboxylic acid or an α, β-unsaturated dicarboxylic acid.

9. A method according to claim 1 wherein said fluoroaluminosilicate glass powder has from 10 to 25% by weight of $Al^{3+}$, from 5 to 30% by weight of $Si^{4+}$, from 1 to 30% by weight of $F^-$, from 0 to 20% by weight of $Sr^{3+}$, from 0 to 20% by weight of $Ca^{2+}$ and from 0 to 10% by weight of an alkali metal ion, based on the total weight of said fluoroaluminosilicate glass powder and wherein said polycarboxylic acid is a homopolymer or copolymer of an acid selected from the group consisting of acrylic acid, methacrylic acid, 2-chloroacrylic acid, 3-chloroacrylic acid, aconitic acid, mesaconic acid, maleic acid, itaconic acid, fumaric acid, glutaconic acid and citraconic acid.

* * * * *